United States Patent
Horvath et al.

(10) Patent No.: US 9,023,018 B2
(45) Date of Patent: May 5, 2015

(54) SURGICAL LASER SYSTEM WITH REMOTE CONTROL FUNCTIONALITY

(75) Inventors: Christopher Horvath, Desert Hot Springs, CA (US); Laszlo Otto Romoda, San Clemente, CA (US)

(73) Assignee: Novartis AG, Basel (CH)

( * ) Notice: Subject to any disclaimer, the term of this patent is extended or adjusted under 35 U.S.C. 154(b) by 376 days.

(21) Appl. No.: 12/634,150

(22) Filed: Dec. 9, 2009

(65) Prior Publication Data

US 2010/0145320 A1 Jun. 10, 2010

Related U.S. Application Data

(63) Continuation of application No. 11/479,636, filed on Jun. 30, 2006, now abandoned.

(51) Int. Cl.
*A61B 18/20* (2006.01)
*A61F 9/008* (2006.01)

(52) U.S. Cl.
CPC ....... *A61F 9/008* (2013.01); *A61F 2009/00872* (2013.01)

(58) Field of Classification Search
CPC . A61F 9/008; A61F 9/00802; A61F 9/00821; A61F 9/00825; A61F 17/00; A61F 2017/00212
USPC .............. 606/4–6, 10–12; 607/88–91, 93–95; 128/898
See application file for complete search history.

(56) References Cited

U.S. PATENT DOCUMENTS

| | | | |
|---|---|---|---|
| 6,129,722 A | 10/2000 | Ruiz | |
| 6,139,542 A * | 10/2000 | Hohla | 606/5 |
| 6,908,461 B2 | 6/2005 | Momiuchi et al. | |
| 2003/0208189 A1 | 11/2003 | Payman | |
| 2005/0245909 A1 | 11/2005 | McCary | |
| 2006/0116667 A1* | 6/2006 | Hamel et al. | 606/1 |

FOREIGN PATENT DOCUMENTS

| WO | 02/083041 A1 | 10/2002 |
|---|---|---|
| WO | 2005/110303 A1 | 11/2005 |

* cited by examiner

*Primary Examiner* — Ahmed Farah
(74) *Attorney, Agent, or Firm* — Jason Finch

(57) ABSTRACT

Embodiments of the present invention provide a laser surgical system with a basic set of functionality which is remotely controllable to implement an advanced set of functionality. According to one embodiment of the present invention, a basic laser surgical system may be coupled to an advanced control unit such that the basic laser surgical system may be controllable by the advanced control unit to implement a broader set of functionality. By moving less frequently used functionality to an advanced unit, the basic unit may be streamlined with regards to both cost and size, and the learning curve required to utilize the basic unit may be reduced relative to a more feature-ladened unit, allowing the basic unit to be utilized in myriad situations or procedures where an "all-in-one" unit would be less than desirable.

6 Claims, 4 Drawing Sheets

SURGICAL LASER SYSTEM WITH REMOTE CONTROL FUNCTIONALITY

This application is a continuation of U.S. patent application Ser. No. 11/479,636 filed on Jun. 30, 2006 now abandoned.

TECHNICAL FIELD OF THE INVENTION

The present invention relates to surgical devices. More particularly, the present invention relates to surgical laser systems used in ophthalmic surgical systems. Even more particularly, the present invention relates to surgical laser systems remotely controllable to implement additional functionality.

BACKGROUND

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. In any case, the surgical instrumentation often implements a whole host of functionality which may be used in the implementation of a wide variety of surgical procedures.

Laser surgery to the retina is the standard of care in the treatment of numerous ophthalmic diseases. Diseases treated by laser photocoagulation include proliferative diabetic retinopathy, diabetic macular edema, cystoid macular edema, retinal vein occlusion, choroidal neovascularization, central serous chorioretinopathy, retinal tears, and other lesions.

As may be imagined, the complexities of these types of retina surgeries may be quite variegated, and concomitantly, the surgical devices used to conduct these surgeries may need to implement a whole host of functionality associated with these surgeries. Often, a surgical laser system may be operable to implement functionality associated with multiple types of surgeries or other procedures, such that one surgical laser system may be used in multiple types of operations or procedures. In many cases, however, these "all-in-one" type of solutions typically have prices which are commensurate with their functionality, in other words they may be quite expensive.

Often, however, customers may not require all the functionality that these all-in-one designs provide. Therefore, these types of designs may be cost prohibitive, more difficult to operate or wasteful of resources. In particular it may be desirable to have simpler lower cost units which may facilitate their use in places where the use of all-in-one designs (i.e. wide degree of functionality in a single unit) may be fiscally or physically impractical, such as use in disaster or rural areas, poorer communities or countries, etc. However, the laser (or other physical components or software) used in such a lower cost unit may be substantially the same as those employed in an "all-in-one" unit. Thus, for those that have need of both a lower cost unit and an "all-in-one" unit, or for those that desire to upgrade from a lower cost unit to an "all-in-one" unit, it is undesirable to pay for duplicate functionality or systems.

Therefore, a need exists for a laser surgery unit operable to implement a basic set of functionality which may be remotely controlled to implement a more advanced set of functionality.

SUMMARY OF THE INVENTION

Embodiments of the present invention provide a laser surgical system with a basic set of functionality which is remotely controllable to implement an advanced set of functionality.

According to one embodiment of the present invention, a laser surgical unit operable to implement one set of functionality may be coupled to an advanced control unit such that the laser surgical unit may be controllable by the advanced control unit to implement a different set of functionality. This set of functionality may include more complicated functionality than the laser surgical unit can implement in a standalone configuration.

Thus by moving the ability to implement certain functionality to an advanced unit embodiments of the present invention provide the advantage that the basic unit may be streamlined with regards to both cost and size, and the learning curve required to utilize the basic unit may be reduced relative to more complicated units allowing the basic unit to be utilized in myriad situations or procedures where an all-in-one unit would be complexity, cost, or size, prohibitive.

Similarly, embodiments of the present invention may provide the advantage that, since a basic unit may be utilized in the implementation of more complex functionality, there is no need to duplicate the functionality or capabilities of the basic unit when implementing this advanced functionality. This may be advantageous to users of such laser surgical systems as they may able to purchase a basic unit at a lower initial price and have a cost effective upgrade path to advanced functionality which does not render the basic unit redundant.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the FIGURES, like numerals being used to refer to like and corresponding parts of the various drawings.

Embodiments of the present invention provide a laser surgical system having a basic set of functionality, which is remotely controllable to implement an advanced set of functionality. According to one embodiment of the present invention, a laser surgical system (e.g. basic unit) operable to implement a basic set of functionality, such as main laser parameter settings, and having minimal customization features, minimal system statistics and diagnostics, etc., may be coupled to another unit (e.g. advanced control unit) such that the basic laser surgical system may be controllable by the advanced control unit to implement, or allow, a broader set of functionality to be implemented through the advanced control unit, such as pre-operation picture viewing, creating custom marked treatment pictures, creating and printing patient record, advanced customizations, doctor log in to activate custom settings, creating and firing custom laser pulse sequences, E-connectivity through an Ethernet port or wireless communication of diagnostics, statistics, service needs or to upload software upgrades, wireless RFID check in for the doctor and customer, etc.

In other words, in certain embodiments a laser surgical system may be controlled by another unit (i.e. remotely controlled) to implement greater functionality than the laser surgical system is capable of implementing as a standalone device. By moving less frequently used functionality to an advanced unit, the basic unit may be streamlined with regards to both cost and size, and the learning curve required to utilize the basic unit may be reduced relative to an "all-in-one" unit, allowing the basic unit to be utilized in myriad situations or procedures where an "all-in-one" unit would be complexity, cost, or size, prohibitive. By the same token, however, since a basic unit may be utilized in the implementation of more complex functionality, there is no need to duplicate the functionality or capabilities of the basic unit when implementing advanced functionality. This may be advantageous to users of such laser surgical systems as they may able to purchase a basic unit at a lower initial price and have a cost effective upgrade path to advanced functionality which does not render the basic unit redundant.

Figure 1:
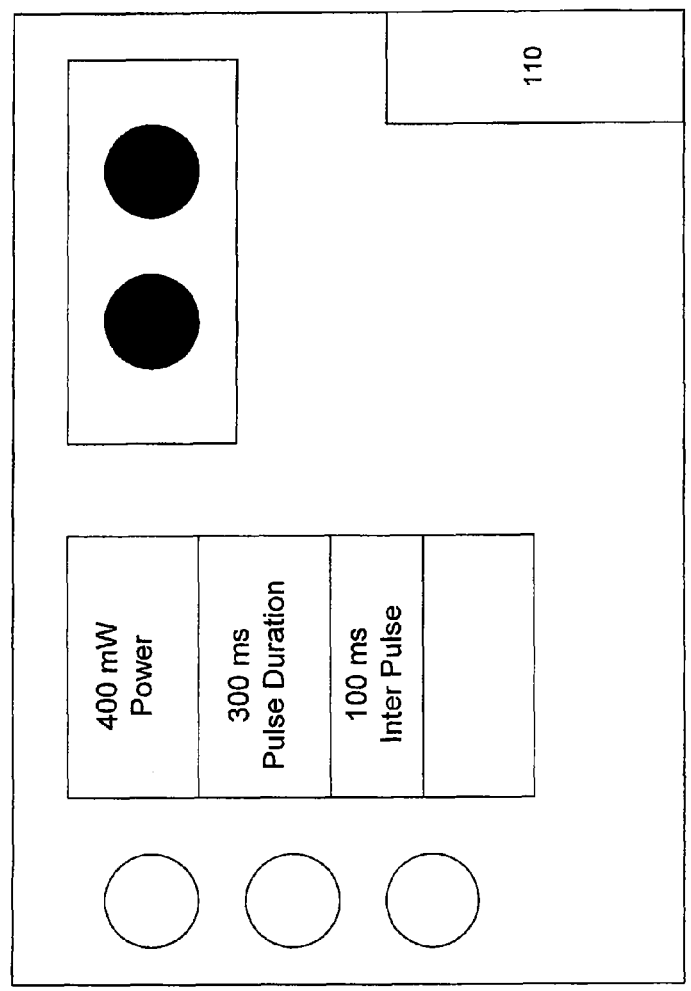
FIG. 1 is a diagrammatic representation of one embodiment of a laser surgical system.

FIG. 1 is a diagrammatic representation of one embodiment of a laser surgical unit with basic functionality. Basic laser surgical unit 100 may comprise a laser and associated control software such that basic laser surgical unit 100 may be operable to implement a basic set of functionality such as that discussed above. It will be understood that, in this context, basic functionality is measured relative to the functionality which may be implemented with the basic laser surgical unit 100 in conjunction with an advanced control unit (discussed in more detail below). Thus, embodiments of basic laser surgical unit 100 may provide a lower cost, entry level laser system with a basic set of functionality particularly well suited to operating room or office use, use in field applications, etc.

In one embodiment, basic laser surgical unit 100 may have a laser similar to that of the Alcon EyeLite Photocoagulator and associated software operable to allow a basic set of functionality to be implemented using basic laser surgical unit 100. Basic laser surgical unit 100 may also comprise communications port 110, allowing basic laser surgical unit 100 to be coupled to an advanced control unit such that basic laser surgical unit 100 may be controlled by the advanced control unit (i.e. remotely controlled) to implement advanced functionality (i.e. a more advanced or different set of functionality than may be implemented with basic laser surgical unit 100 alone).

Figure 2:
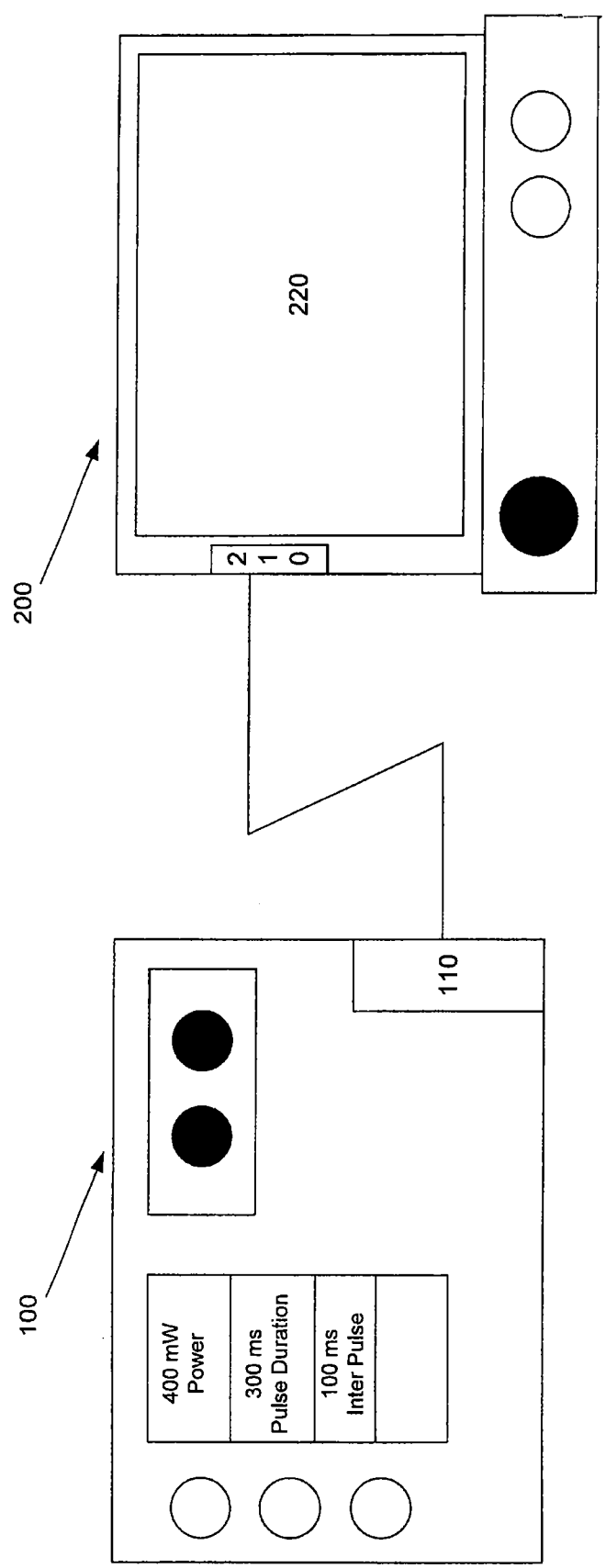
FIG. 2 is a diagrammatic representation of one embodiment of a laser surgical system coupled to a control unit.

This coupling arrangement may be better described with reference to FIG. 2, which depicts one embodiment of a basic laser surgical unit 100 coupled to an advanced control unit 200. In one embodiment, basic laser surgical unit 100 and advanced control unit 200 may be coupled to one another through communications ports 110, 210 on basic laser surgical unit 100 and advanced control unit 200, respectively. Advanced control unit 200 can include software (e.g. instructions on a computer readable medium) and a microprocessor such that advanced control unit 200 is operable to control basic laser surgical unit 100 or components thereof (e.g. the laser of basic laser surgical unit 100) to implement a higher or advanced level of functionality (e.g. more or advanced features) than basic laser surgical unit 100 is operable to implement in a standalone configuration.

In some embodiments, the software and/or microprocessor of advanced control unit 200 may also be operable to implement (e.g. duplicate) the functionality which basic laser surgical unit 100 is operable to implement in a standalone configuration, such that basic laser surgical unit 100 can be controlled by advanced control unit 200 in order to implement both the basic set of functionality and the advanced set of functionality (e.g. the set of functionality which can be implemented utilizing advanced control unit 200 and basic surgical unit 100 is a superset of the functionality which can be implemented using basic surgical unit 100 in a standalone configuration). To that end, advanced control unit 200 may also comprise user interface 220, which may, in turn, include a touch screen. This touch screen may serve as an interface through which an operator may select or control the functionality implemented by the combination of advanced control unit 200 and basic laser surgical unit 100.

Figure 3:
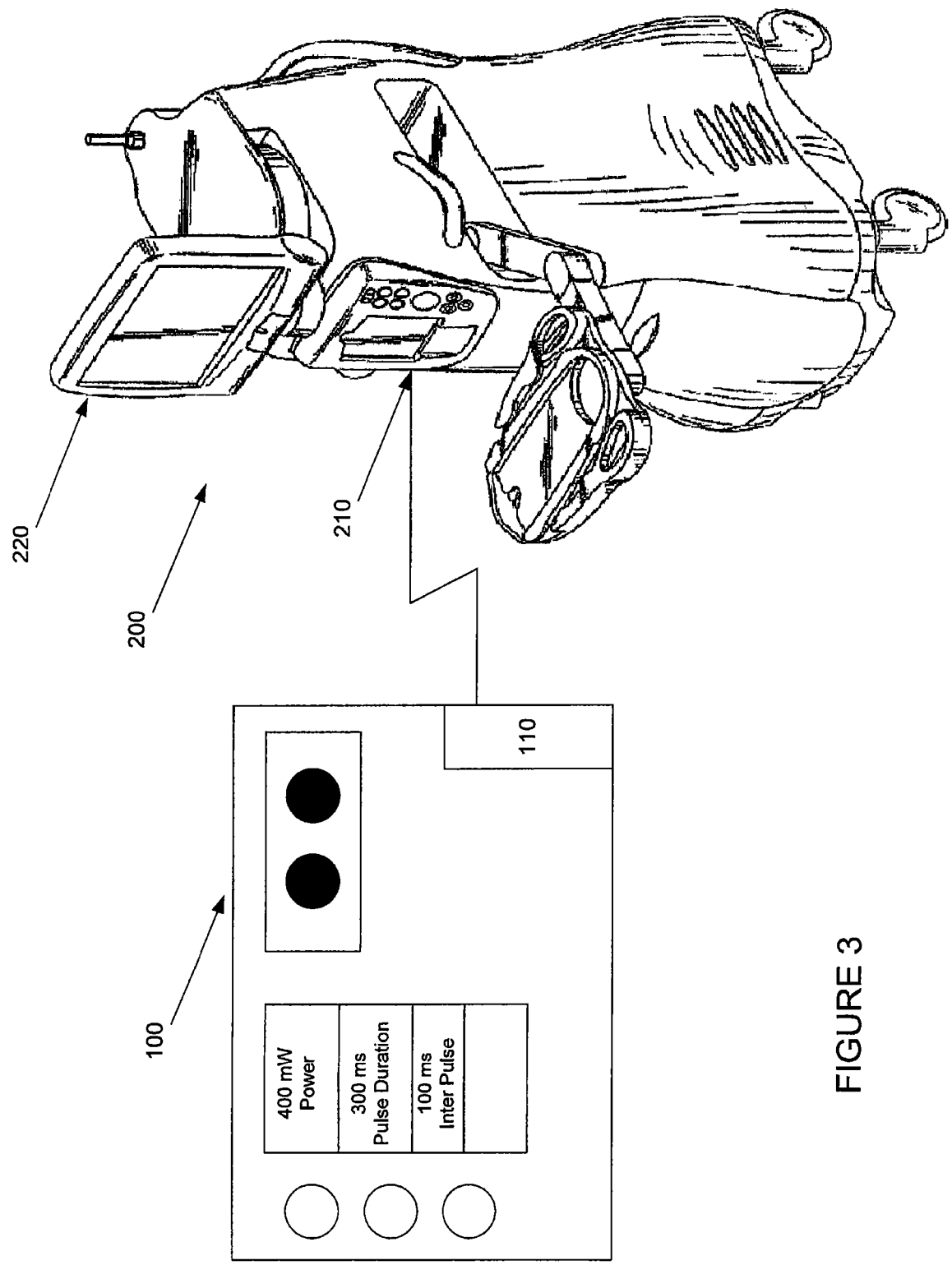
FIG. 3 is a diagrammatic representation of one embodiment of a laser surgical system coupled to a control unit.

Moving to FIG. 3, another arrangement by which the functionality of a basic laser surgical unit 100 can be increased by coupling it to an advanced control unit 200 is depicted. In this embodiment, advanced control unit 200 may comprise a surgical console similar to the Series 2000® Legacy® cataract surgical system, the Accurus® 400VS surgical system, and/or the Infiniti™ Vision System surgical system, all available from Alcon Laboratories Inc. of Fort Worth, Tex., and can include a connection panel used to connect various tools and consumables to the surgical console. The connection panel can include, for example, a coagulation connector, balanced salt solution receiver, connectors for various hand pieces and a fluid management system ("FMS") or cassette receiver. A surgical console can also include a variety of user friendly features, such as a foot pedal control (e.g., stored behind a panel) and other features. Advanced control unit 200 may also include swivel monitor 220 which can be positioned in a variety of orientations for whomever needs to see the touch screen of the swivel monitor. Swivel monitor 220 can swing from side to side, as well as rotate and tilt. A graphical user interface ("GUI") that allows a user to interact with console 100 may be provided or presented on the touch screen of swivel monitor 220.

Figure 4:
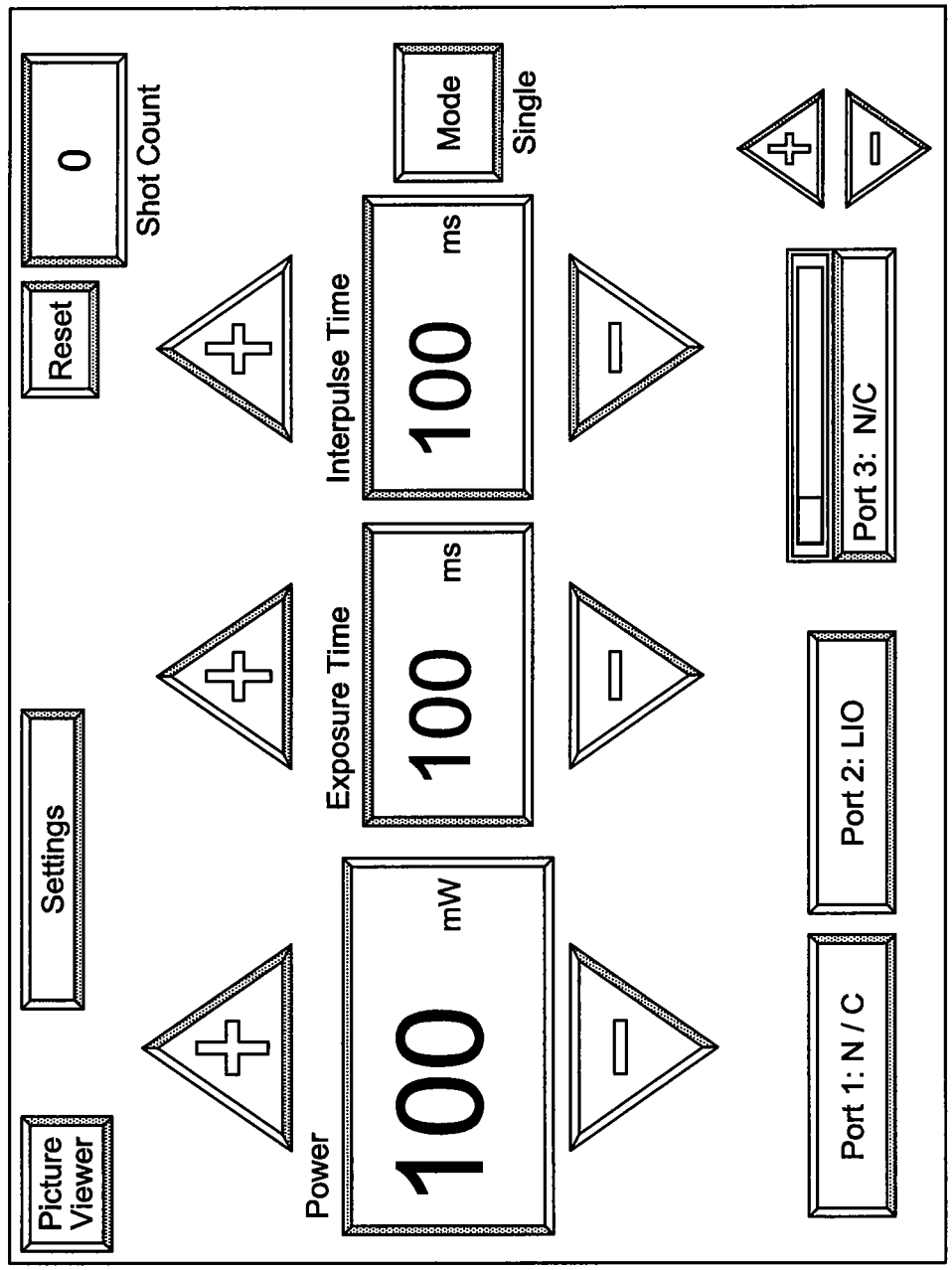
FIG. 4 is a diagrammatic representation of one embodiment of a graphical user interface.

As discussed above, advanced control unit 200 may comprise communications port 210, through which advanced control unit 200 may be coupled to basic laser surgical unit 100 (e.g. advanced control unit 200 and basic laser surgical unit 100 may communicate through communication ports 110 and 210) and advanced control unit 200 includes software and/or a microprocessor such that advanced control unit 200 is operable to control basic laser surgical unit 100 to implement a more advanced set of features than basic laser surgical unit 100 is operable to implement in a standalone configuration. Thus, in one embodiment, utilizing a GUI provided on the touch screen of swivel monitor 220, an operator may control the combination of advanced control unit 200 and basic laser surgical unit 100 to implement advanced functionality which basic laser surgical unit 100 may be incapable of implementing in a standalone configuration. One example of such a graphical user interface is depicted in FIG. 4.

It will be apparent after reading this disclosure that the coupling between basic laser unit 100 and advanced control unit 200 may be accomplished via any suitable coupling mechanism and/or protocol. More particularly, communication between the basic laser unit 100 and advanced control unit 200 may occur via a wired or wireless interfaces, such that basic laser unit 100 is coupled to advanced control unit 200 through a cable or via wireless communication. Advanced control unit 200 may, alternatively, have a set of slots such that the basic laser surgical unit 100 may "plug-in" to a spot in the chassis of an advanced control unit 200 (for example, through a backplane interface present in advanced control unit 200). In one particular embodiment, communication ports 110 and 210 may be Ethernet ports, as will be known to those having ordinary skill in the art.

It may be imagined, however, that in many cases basic laser surgical unit 100 and advanced control unit 200 may be sensitive devices, and may comprise components (e.g. lasers) which could pose a danger if they are improperly utilized. Consequently, it may not be desirable to utilize a standard protocol which can be easily learned and taken advantage of to manipulate basic laser surgical unit 100 or advanced control unit 200 without proper training or authorization. Therefore, in some embodiments a standard connector may be utilized (e.g. an Ethernet connector) for communications ports 110, 210; however a variation may be implemented on this standard connector to implement proprietary communications between basic laser surgical unit 100 and advanced control unit 200. For example, one or more pins of the Ethernet connectors comprising communications port 110 and 210 may be scrambled (e.g. lines between the two communication port 110, 210 may connect to pins in locations other than those specified according to the standard Ethernet protocol, or pins of communication port 110, 210 may be utilized for non standard purposes). In addition to preventing unauthorized control of basic laser surgical unit 100 or advanced control unit 200, these types of scrambling arrangements may allow basic laser surgical unit 100 or advanced control unit 200 to detect the coupling of improper or incompatible devices, or improper attempts at control or communication, and take appropriate remedial action, such as logging the improper access, shutting down, sounding an alarm, etc.

Thus, by allowing communication between a basic laser surgical unit and an advanced control unit, embodiments of the present invention provide a laser surgical unit with a basic set of functionality which is remotely controllable to implement an advanced set of functionality. By moving less frequently used functionality to an advanced unit the basic unit may be streamlined with regards to both cost and size, and the learning curve required to utilize the basic unit may be reduced relative to a more function-ladened system, allowing the basic unit to be utilized in myriad situations or procedures where an "all-in-one" unit would be less than desirable. Moreover, since a basic unit may be utilized in the implementation of more complex functionality, there is no need to duplicate the functionality or capabilities of the basic unit when implementing advanced functionality.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

The invention claimed is:

1. A remotely controllable laser surgical system, comprising:
   a laser surgical unit comprising a photocoagulator, the laser surgical unit comprising an ophthalmic laser and a first microprocessor configured to execute a basic set of software instructions to implement a first set of functionality, the first set of functionality comprising functionality for one or more laser parameter settings for the photocoagulator;
   an external control unit comprising an advanced set of software instructions to control the laser surgical unit to implement a second set of functionality, the second set of functionality comprising functionality to create a laser pulse sequence for photocoagulation and to fire the laser pulse sequence, at least some of the second set of functionality distinct from the first set of functionality; and
   a communication port configured to receive a control signal from the external control unit that allows the external control unit to control the laser surgical unit.

2. The remotely controllable laser surgical system of claim 1, wherein the laser surgical unit cannot perform at least some of the second set of functionality independent of the external control unit.

3. The remotely controllable laser surgical system of claim 2, wherein the second set of functionality is a superset of the first set of functionality.

4. The remotely controllable laser surgical system of claim 2, wherein the communication port is an Ethernet port.

5. The remotely controllable laser surgical system of claim 4, wherein a set of pins of the communication port is scrambled.

6. The remotely controllable laser surgical system of claim 1, wherein the laser surgical unit is operable to detect when an incompatible device is coupled to the communication port.

* * * * *